(12) United States Patent
Lancial et al.

(10) Patent No.: US 8,419,774 B2
(45) Date of Patent: Apr. 16, 2013

(54) ATTACHMENT DEVICES AND METHODS FOR SPINAL IMPLANTS

(75) Inventors: Michael E. Lancial, St. Louis Park, MN (US); Hugh Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 9 days.

(21) Appl. No.: 13/031,989

(22) Filed: Feb. 22, 2011

(65) Prior Publication Data

US 2011/0144696 A1   Jun. 16, 2011

Related U.S. Application Data

(63) Continuation of application No. 11/833,683, filed on Aug. 3, 2007, now Pat. No. 7,892,267.

(51) Int. Cl.
*A61B 17/88* (2006.01)

(52) U.S. Cl.
USPC .......................................... 606/279; 606/247

(58) Field of Classification Search .... 606/60.65–67.95, 606/104, 246–249, 279, 300–321; 623/17.11, 623/20.17, 23.27, 23.3, 23.48, 23.55
See application file for complete search history.

(56) References Cited

U.S. PATENT DOCUMENTS

| | | | |
|---|---|---|---|
| 5,443,515 A | 8/1995 | Cohen et al. | |
| 5,984,926 A | 11/1999 | Jones et al. | |
| 6,063,442 A | 5/2000 | Cohen et al. | |
| 6,146,384 A | 11/2000 | Lee et al. | |
| 6,214,012 B1 | 4/2001 | Karpman et al. | |
| 6,890,335 B2 | 5/2005 | Grabowski et al. | |
| 6,955,677 B2 | 10/2005 | Dahners | |
| 7,591,851 B2 * | 9/2009 | Winslow et al. | 623/17.11 |
| 2004/0220575 A1 | 11/2004 | Biedermann et al. | |
| 2006/0085068 A1 * | 4/2006 | Barry | 623/17.11 |
| 2006/0241776 A1 | 10/2006 | Brown et al. | |
| 2007/0055373 A1 | 3/2007 | Hudgins et al. | |
| 2007/0112428 A1 | 5/2007 | Lancial | |
| 2007/0156145 A1 | 7/2007 | Demakas | |

FOREIGN PATENT DOCUMENTS

| | | |
|---|---|---|
| DE | 4142584 A1 | 6/1993 |
| DE | 10319781 B3 | 8/2004 |

OTHER PUBLICATIONS

Zimmer, Inc. Trabecular Metal Family: A Guide for Patients, online product information found at www.zimmer.com dated Oct. 24, 2005 (3 pages).

* cited by examiner

*Primary Examiner* — Eduardo C Robert
*Assistant Examiner* — Christina Negrellirodriguez
(74) *Attorney, Agent, or Firm* — Seager Tufte & Wickhem LLC

(57) ABSTRACT

A system for the treatment of a spine generally comprises an implant and an attachment device for securing the implant to a portion of a patient's bone. A first portion of the attachment device is sized for insertion into a hole in the bone, and a second portion of the attachment device is configured to be received in an opening of the implant. The first portion comprises a biocompatible material defined by a network of interconnected pores configured promote bone growth into the first portion.

19 Claims, 5 Drawing Sheets

ATTACHMENT DEVICES AND METHODS FOR SPINAL IMPLANTS

REFERENCE TO RELATED APPLICATIONS

This application is a continuation of U.S. patent application Ser. No. 11/833,683, filed Aug. 3, 2007, now U.S. Pat. No. 7,892,267, which is incorporated herein by reference.

FIELD OF THE INVENTION

The present invention relates generally to systems and methods for the treatment of a spine, and more particularly to systems and methods for securing biocompatible implants to a bone of the spine.

BACKGROUND

The spinal column is a highly complex system of bones and connective tissues that provides support for the body and protects the delicate spinal cord. The spinal column includes a series of vertebrae stacked one on top of the other, each vertebral body including an inner or central portion of relatively weak cancellous bone and an outer portion of relatively strong cortical bone. The vertebrae in the cervical, thoracic, and lumbar regions of the spine are separated by intervertebral discs, which serve as cushions between adjacent vertebrae to dampen compressive forces experienced by the spine. A vertebral canal containing the spinal cord is formed by the intervertebral foramen of the vertebrae.

There are many types of conditions that can lead to significant pain and affect movement of the spine. Oftentimes these conditions are treated by securing or more implants to the spine, with the implants being designed to achieve a particular type of treatment. For instance, facet implants are often implanted between the facet surfaces of adjacent vertebrae when it is desired to provide joint spacing, joint stabilization, joint capsule replacement, cushioning and/or an articulating surface for the opposing pair of facets. Examples of such facet implants are disclosed in U.S. patent application Ser. Nos. 11/221,938 and 11/274,385, which are owned by the assignee of the present application and hereby incorporated by reference in their entirety. Other implants include, without limitation: cervical plates, fixation rods, and similar devices.

The implants are typically secured to the spine using one or more bone screws or other attachment members. Other fixation techniques are also used when desired. For example, in some applications the implants are secured using adhesive or sutures. In other applications, the implants are secured by a post cemented into a cavity created in the bone. Although a wide variety of attachment devices and methods exist, there remains room for improvement.

SUMMARY

A system for the treatment of a spine generally comprises an implant and an attachment device for securing the implant to a portion of a patient's bone. A first portion of the attachment device is sized for insertion into a hole in the bone, and a second portion of the attachment device is configured to be received in an opening of the implant. The first portion comprises a biocompatible material defined by a network of interconnected pores configured to promote bone growth into the first portion.

In one embodiment, the hole in the bone may be greater in a first dimension than in a second dimension. The first portion of the attachment device may be rotated when received in the hole to a position that restricts removal of the attachment device from the hole.

In another embodiment, the first portion further includes an inner bore extending therethrough, an outer surface, and a plurality of channels each extending from the outer surface to the inner bore. The channels provide fluid communication from the inner bore to the bone for the delivery of a bone growth promoting material.

In yet another embodiment, the biocompatible material of the first portion has a degree of porosity that approaches that of the bone. The biocompatible material may comprise porous tantalum in some embodiments.

A method of securing an implant to a bone is also provided. The method generally comprises forming a hole in the bone, positioning the implant relative to the bone so that an opening in the implant is in communication with the hole in the bone, and a inserting a first portion of an attachment device through the opening of the implant. The first portion extends into the hole of the bone so that a second portion of the attachment device is then received in the opening of the implant. Again, the first portion of the attachment device may comprise a biocompatible material defined by a network of interconnected pores configured to promote bone growth into the first portion.

In one embodiment, the hole in the bone is formed with an elliptical configuration having a minor axis, a major axis, and a first dimension along the major axis. Additionally, the first portion of the attachment device has an elliptical cross-sectional configuration with a first dimension approximately equal to the first dimension of the hole in the bone and a second dimension less than the first dimension. Inserting the attachment member in such an embodiment may further comprise inserting the first portion into the hole in the bone with the first dimension aligned with the major axis of the hole and the second dimension aligned with the minor axis of the hole.

The hole in the bone and the first portion of the attachment device may be formed with matching elliptical configurations in some embodiments so that the first portion is secured within the hole upon insertion. In other embodiments, the method may further comprise rotating the attachment member relative to the hole after the first portion is inserted therein. The attachment member may be rotated so that the first dimension of the first portion is substantially aligned with the minor axis of the hole and the second dimension of the first portion is substantially aligned with the major axis of the hole.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
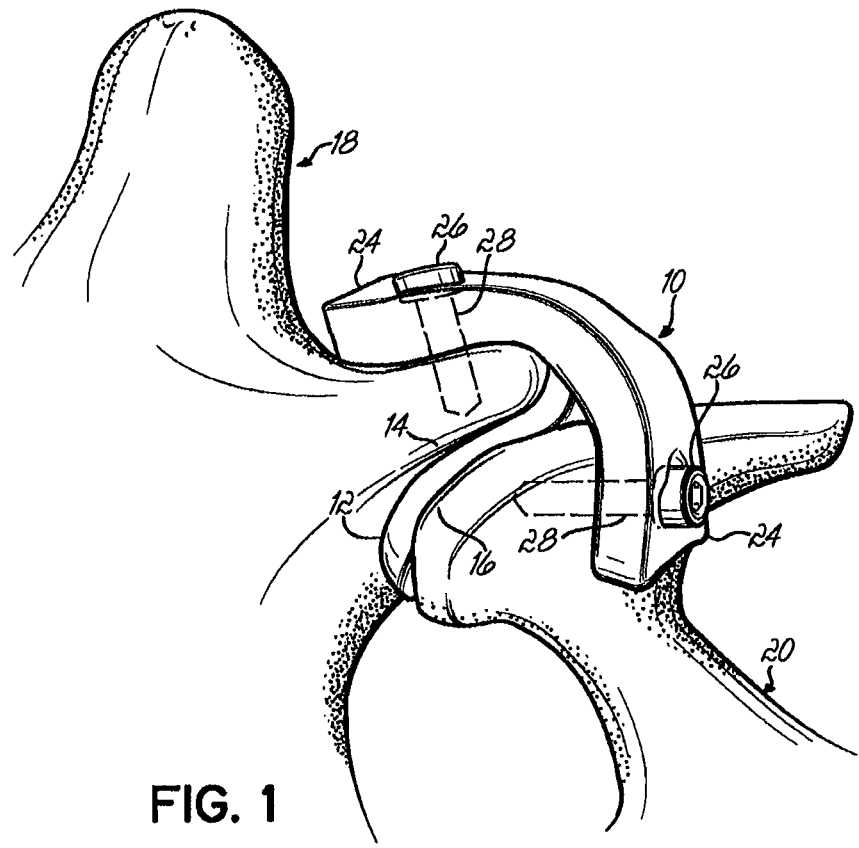
FIG. 1 is a perspective view illustrating an exemplary implant positioned in the facet joint of a spine.

FIG. 1 generally shows one example of an implant 10 that may be used to treat a spinal condition. The implant 10 generally includes a main body 12 positioned between opposed facets 14, 16 of adjacent vertebrae 18, 20 and fixation wings 24 secured to the vertebrae 18, 20 using one or more attachment members 26. Such an arrangement provides the implant 10 with a generally T-shaped configuration, with the fixation wings 24 being bent and/or stretched as needed to conform to each vertebra 18, 20 before being secured by the attachment members 26, which extend through openings 28 in fixation wings 24. The fixation wings 24 exert a retraining force on the vertebrae 18, 20 to help maintain the opposed facets 14, 16 in a desired orientation. Additional details relating to the implant 10 are provided in U.S. application Ser. Nos. 11/221,938 and 11/274,385, the disclosures of which, as indicated above, are fully incorporated herein by reference.

Although the implant 10 will be referenced below when discussing details of attachment members according to the invention, those skilled in the art will appreciate that the invention may equally apply to any biocompatible implant secured to bone. For example, attachment members according to the invention may be used to secure plates and other similar devices to vertebrae of the spine or other bones in a patient's body.

Figure 2:
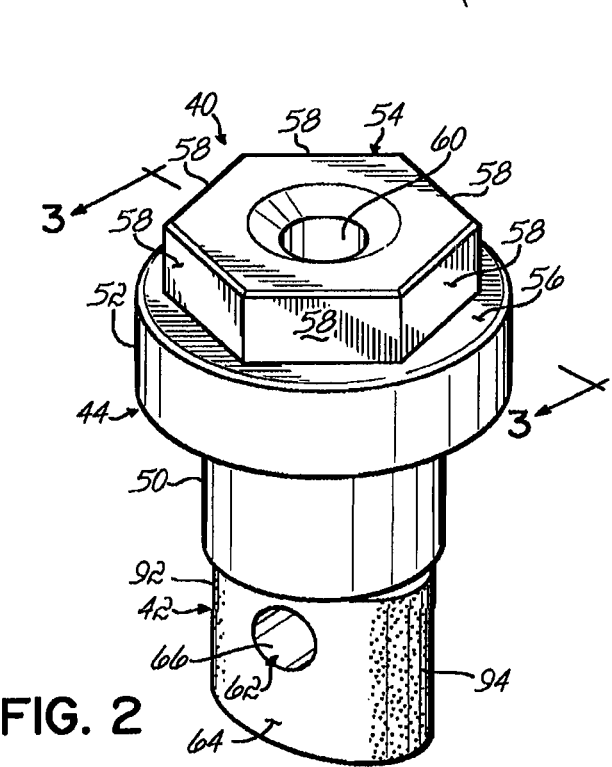
FIG. 2 is a perspective view of an attachment device according to one embodiment of the invention for securing the implant of FIG. 1 to a bone.

With reference to FIG. 2, an attachment device 40 according to one embodiment of the invention includes a first portion 42 and a second portion 44. The second portion 44 may be a separate component mounted on or secured to the first portion 42, or may be integrally formed with the first portion 42 such that the attachment device 40 has a one-piece construction. The embodiment shown has a two-piece construction with the first portion 42 being formed from a porous first material and the second portion 44 being formed by a more rigid second material. To this end, and as set forth in further detail below, the first portion 42 may be formed from a material designed to promote ingrowth of bone whereas the second portion 44 may be formed from a material designed to interface with one of the openings 28 (FIG. 1) in the implant 10.

Figure 3:
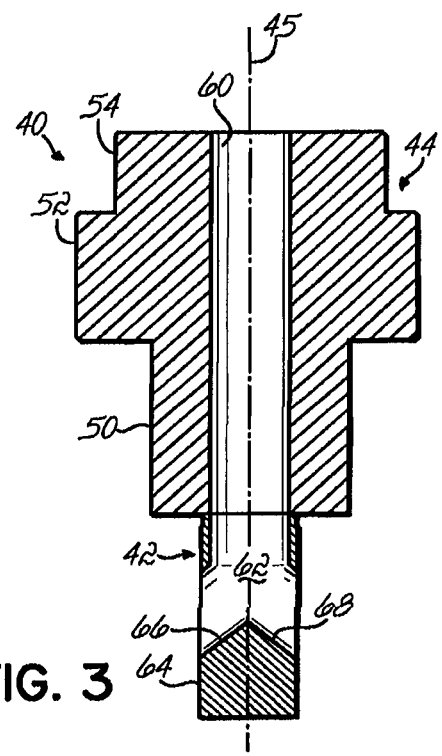
FIG. 3 is a cross-sectional view taken along line 3-3 in FIG. 2.
Figure 5A:
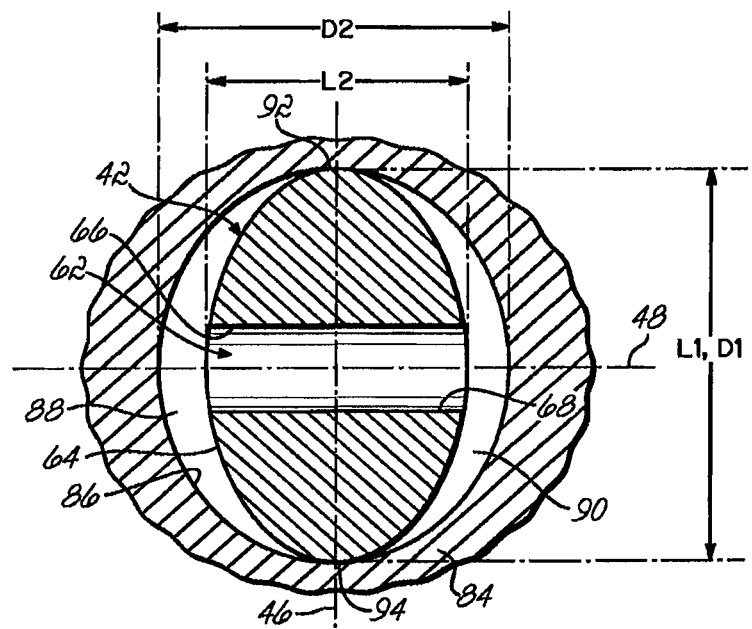
FIGS. 5A and 5B are cross-sectional views illustrating a portion of the attachment device of FIG. 1 being initially secured within a hole in a bone.

As shown in FIGS. 2 and 3, the first portion 42 has a generally oval or elliptical cross-sectional profile when viewed in a plane generally transverse to an axis 45 of the implant 10. Thus, the first portion 42 has a first dimension L1 along a major axis 46 (FIG. 5A) and a second, smaller dimension L2 along a minor axis 48 (FIG. 5A). The second portion 44 includes a first section 50 having a first radial dimension and a flange section 52 having a second radial dimension larger than the first radial dimension. The first radial dimension may or may not be approximately equal to the first dimension L1 of the first portion 42. A fastening section 54 extending from an upper surface 56 of the flange section 52 is shaped so that the attachment device 40 may be gripped or rotated by a tool (not shown). For example, in one embodiment, the fastening section 54 includes straight edges 58 defining a hexagonal structure so that the implant 10 may be rotated by a socket wrench or the like.

The second portion 44 also includes an axial bore 60 extending through the fastening section 54, the flange section 52, and the first section 50. Although the axial bore 60 is shown as being generally cylindrical, other shapes and configurations are possible. For example, if desired, the axial bore 60 may have a hexagonal configuration so that the implant 10 may be rotated with an Allen key (not shown) or similar type of tool. The first portion 42 is provided with an inner bore 62 as well, but the inner bore 62 extends from the axial bore 60 to an outer surface 64 of the first portion 42. Thus, the axial bore 60 and inner bore 62 define a passage extending through the implant 10. In one embodiment, the inner bore 62 is generally in the shape of an inverted Y with a first branch 66 and a second branch 68 extending to respective first and second locations on the outer surface 64. In an alternative embodiment, the inner bore 62 has a substantially T-shaped configuration. In yet another embodiment, the inner bore 62 may extend through the entire longitudinal axis of the attachment device 40.

Figure 4:
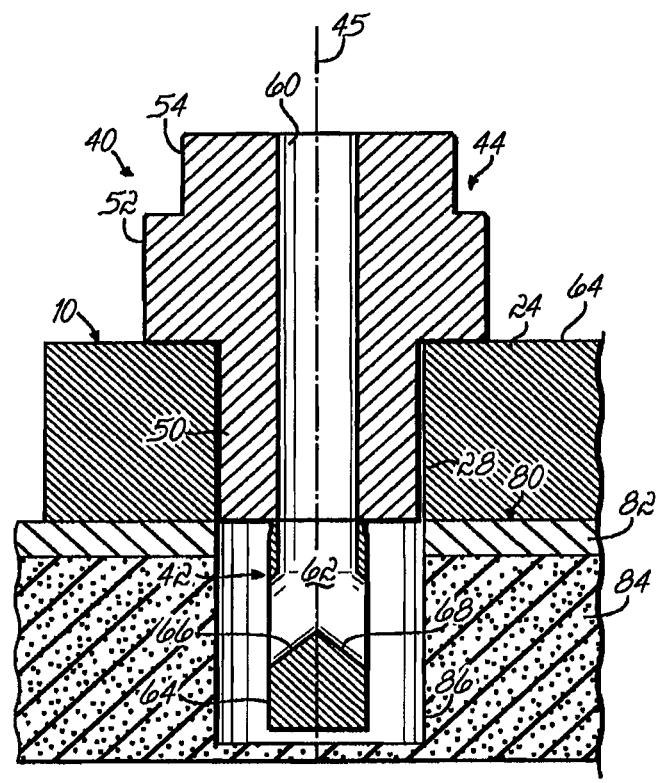
FIG. 4 is a cross-sectional view similar to FIG. 3 showing the attachment device of FIG. 1 inserted into a hole in a bone.

FIG. 4 illustrates the attachment device 40 securing one of the fixation wings 24 to a vertebra 80, which includes a hard, outer layer of cortical bone 82 and inner cavities (not shown) of softer cancellous bone 84 (also referred to as trabecular bone). The first portion 42 is received in a hole 86 formed in the vertebra 80 and is configured to allow bone growth into portions thereof. To this end, the first portion 42 may be constructed from a highly porous material so that the surrounding cancellous bone 84 is able to rapidly and extensively grow into the interconnected pores to secure the attachment device 40 relative to the vertebra 80.

For example, the first portion 42 may be comprised of a biocompatible material having a degree of porosity that approaches that of natural cancellous bone. One example of such a material is Trabecular Metal™ material, which is marketed by Zimmer Spine, Inc., of Edina, Minn. This material is also described in several U.S. patents, including, for example, U.S. Pat. Nos. 5,443,515 and 6,063,442, the disclosure of which are incorporated herein by reference. In addition to having a cellular or highly porous structure that resembles cancellous bone itself, the material of the first portion 42 may have a high compressive strength and low modulus of elasticity comparable to cancellous bone. Because it approximates the physical and mechanical properties of cancellous bone, the material of the first portion 42 is highly conducive to bone formation. Moreover, the material can be fabricated into complex shapes as needed to match a particular implant or hole.

Although the Trabecular Metal™ material marketed by Zimmer Spine is a porous tantalum material fabricated using a vapor deposition technique, those skilled in the art will appreciate that the first portion 42 may alternatively be constructed from other biocompatible materials having a degree of porosity similar to that of natural cancellous bone. These other materials may include metallic materials (pure metals and/or alloys) other than tantalum, or porous ceramic materials having the appropriate physical and mechanical properties.

When the first portion 42 is received in the hole 86, the first section 50 of the second portion 44 is received and positioned in the opening 28 of the fixation wing 24. The flange section 52 remains positioned against an outer surface 64 of the fixation wing 24 to help retain the implant 10 against the vertebra 80. As can be appreciated, such an arrangement is merely one example of how the second portion 44 may be shaped to retain the implant 10 when the first portion 42 is secured relative to the vertebra 80. A wide variety of other shapes are possible for both the second portion 44 and opening 28, as long as the second portion 44 has a portion with a radial dimension larger than the smallest dimension of the opening 28. Additionally, because the second portion 44 interacts with the implant 10 rather than the cortical bone 82 and cancellous bone 84, it need not be formed from the same material as the first portion 42. The second portion 44 may instead be formed from a different biocompatible material designed to reduce cost and withstand wear.

A method of securing the implant 10 to the vertebra 80 with the attachment device 40 will now be described. The hole 86 is first formed in the vertebra 80 by drilling or any other suitable technique. The implant 10 is then positioned relative to the vertebra 80 and one of the openings 28 is aligned with the hole 86 so that the attachment device 40 may be inserted therethrough to secure the implant 10. Due to its highly porous nature, it is desirable to insert the first portion 42 through the opening 28 in the implant 10 and into the hole 86 in the vertebra 80 without a significant amount of contact between the outer surface 64 and the cortical bone 82 and cancellous bone 84. If the outer surface 64 scrapes against the cortical bone 82 or cancellous bone 84 as it is inserted into the hole 86, the pores may become clogged or their spongy structure may otherwise become compromised, which diminishes the ability of the first portion 42 to allow bone ingrowth.

Figure 5B:
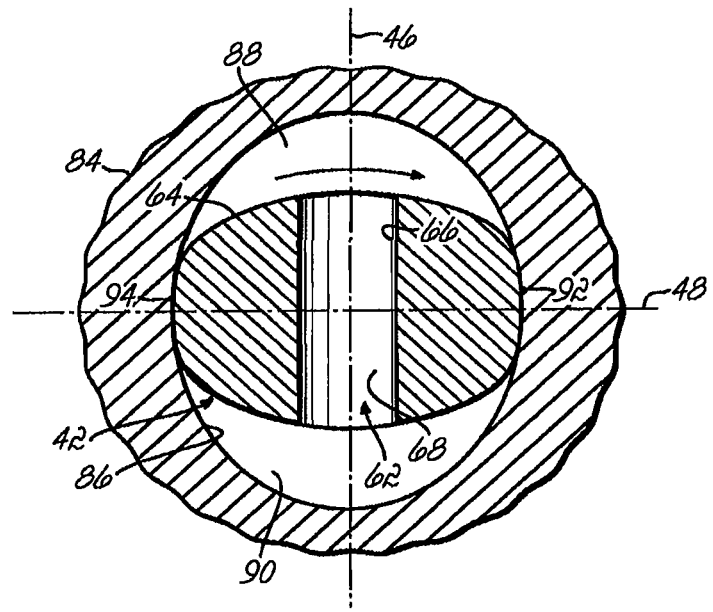

Advantageously, the hole 86 may be formed with a shape that substantially corresponds to the shape of the first portion 42. FIGS. 5A and 5B schematically illustrate the hole 86 and first portion 42 in the cancellous bone 84.
The hole 86 has a substantially elliptical shape with a first dimension D1 along the major axis 46 approximately equal to the first dimension L1 of the first portion 42 and a second dimension D2 along the minor axis 48 slightly larger than the second dimension L2 of the first portion 42 (but still smaller than the dimension L1 along the major axis 46). As a result of this arrangement, the first portion 42 cannot be inserted into the hole 86 until the first dimension L1 is aligned along the major axis 46 and the second dimension L2 is aligned along the minor axis 48. Additionally, the second portion 44 may have a cross-sectional dimension equal to or greater than the second dimension D2 so that it does not extend through the implant 10 and into the hole 86. Spaces 88, 90 maintained between outer surface 64 and hole 86 on opposite sides of major axis 46 help protect the porous structure of the first portion 42 from becoming clogged or compromised from contact with the cancellous bone 84.

The hole 86 may be designed to create a slight interference fit with a first bone-engaging surface 92 and a second bone-engaging surface 94 of the first portion 42 along the major axis 46 to initially secure the attachment device 40 relative to the vertebra 80. Only the first bone-engaging surface 92 and second bone-engaging surface 94 contact the cancellous bone 84 such that the effect of this contact on the porous structure of the second portion 44 is limited to small, localized areas. Once the first portion 42 is positioned within the hole 86, a surgeon may then rotate the attachment device 40 relative to the vertebra 80 to increase the amount of interference between the hole 86 and the first portion 42. This rotation will typically be accomplished by using a tool configured to grip the fastening section 54 of the second portion 44.

As shown in FIG. 5B, when the attachment device 40 is rotated approximately 90°, the first bone-engaging surface 92 and second bone-engaging surface 94 become substantially aligned along the minor axis 48 and the spaces 88, 90 become aligned along the major axis 46. Because the second dimension D2 of the hole 86 is less than the first dimension D1, the first portion 42 is forced into further compression to secure the attachment device 40. Upon rotation, the first portion 42 may deform the cancellous bone 84. And because the first dimension D1 of the hole 86 is larger than the second dimension D2, the spaces 88, 90 increase in size so as to define larger voids between the first portion 42 and cancellous bone 84.

In some embodiments, the second portion 44 rotates with the first portion 42 when securing the attachment device 40. In other embodiments, the first portion 42 may be rotatingly attached to the second portion 44 so that the second portion need not rotate with the first portion 42. For example, an instrument (not shown) designed to engage the first portion 42 may be inserted through the axial bore 60 of the second portion 44. Once engaged with the first portion 42, the instrument may be then be rotated to cause the first portion 42 to rotate relative to the second portion 44 and to secure the attachment device 40 within the hole 86.

Once the first portion 42 is inserted into the hole 86 and before, during, or after the rotation of the attachment device 40, the spaces 88, 90 may be filled with a material configured to promote the growth of bone into the porous structure of the first portion 42. For example, morselized bone or bone morphogenetic protein (BMP) may be packed into the spaces 88, 90. Advantageously, the morselized bone or BMP may be delivered to the spaces 88, 90 through the axial bore 60 and inner bore 62. The surgeon's ability to place this material through the inner bore 62 to the spaces 88, 90 improves following the rotation of the first portion 42 as the spaces 88, 90 increase in size to define larger voids.

Figure 6:
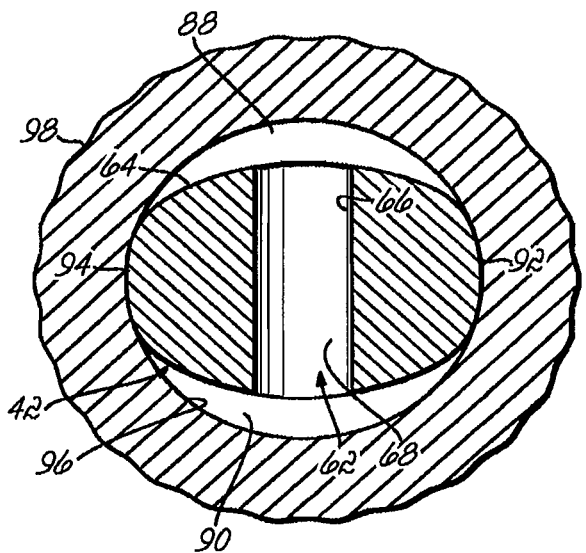
FIG. 6 is a cross-sectional view illustrating a portion of an attachment device according to another embodiment of the invention secured within a hole in a bone.

In alternative embodiments, the first portion 42 does not need to be rotated to secure the attachment device 40 to a hole in a bone. For example, as shown in FIG. 6, the first bone-engaging surface 92 and second bone-engaging surface 94 may be designed to create an interference fit with a hole 96 in a bone 98 upon inserting the first portion 42 into the hole 96. The remainder of the outer surface 64 of the first portion 42 is not in engagement with the bone 98, and bone growth-promoting material may still be delivered through the inner bore 62 without obstruction. Thus, in such an embodiment, the hole 96 may be any shape that allows for the creation of the interference fit.

Even though the first portion 42 may not need to be rotated in FIG. 6 to secure the attachment device 40 within the hole 96, there may be instances when such rotation facilitates insertion of the first portion 42 into the hole 96. For example, in some embodiments, the hole 96 may have a circular cross-sectional configuration and the first bone-engaging surface 92 and/or second bone-engaging surface 94 may include threads (not shown). After aligning the first portion 42 with the hole 96 and initially engaging the bone 98, the first portion 42 may be rotated and driven further into the hole 96 by the threads to secure the attachment device 40. The first bone-engaging surface 92 and second bone-engaging surface 94 are the only portions of the outer surface 64 that come into contact with the bone, thus leaving the remaining porous material of the first portion 42 unclogged and free to facilitate bone in-growth.

Due to the highly porous nature of the material forming the first portion 42, bone is able to rapidly grow into the first portion 42 to fuse the attachment device 40 to the vertebra 80. In one embodiment, the first portion 42 is comprised of a structural biomaterial that is at least 70% porous. In another embodiment, the first portion 42 is comprised of a structural biomaterial, such as Trabecular Metal™ material, that is at least 80% porous. The bone-like physical and mechanical properties of Trabecular Metal™ material contribute to extensive bone infiltration so that the attachment device 40 is strongly attached to the vertebra 80.

Figure 7:
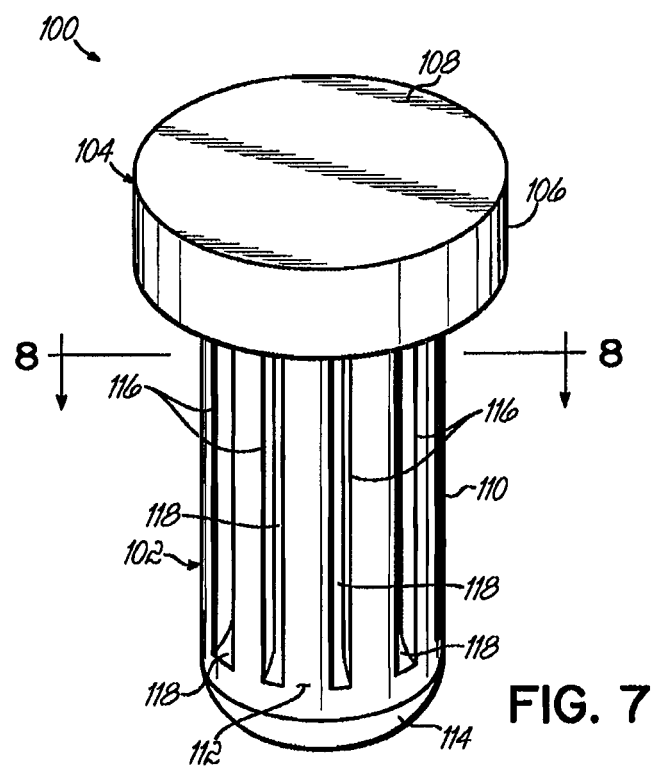
FIG. 7 is a perspective view of an attachment device according to alternative embodiment of the invention.

FIG. 7 illustrates an attachment device 100 according to an alternative embodiment of the invention. Like the attachment device 40, the attachment device 100 includes a first portion 102 and a second portion 104, with at least the first portion 102 being formed from a material having a degree of porosity that approaches that of natural bone. The second portion 104 may also be formed from a material that has a degree of porosity that approaches that of natural bone. For example, in one embodiment, both the first portion 102 and second portion 104 may be constructed from Trabecular Metal™ material. In another embodiment, the first portion 104 may be constructed from a first material with a first porosity and the second portion 102 may be constructed from a second material with a second porosity less than the first porosity.

The second portion 104 includes a flange section 106 that operates in the same manner as the flange section 52. If desired, the second portion 104 may also be provided with a fastening section (not shown) that operates in the same manner as the fastening section 54. Accordingly, reference can be made to the description of the embodiment in FIGS. 2-4 for an understanding of the second portion 104. Although a section similar to the first section 50 is not provided on the second portion 104, it will be appreciated that the second portion 104 may be formed with such a section if desired.

The first portion 102 is generally cylindrical in nature and includes a main body section 110 having an outer surface 112 and a bottom section 114. One or more grooves 116 may be provided in the outer surface 112 so that groove surfaces 118 are recessed relative to the outer surface 112. Such an arrangement protects the groove surfaces 118 from contact with bone when the attachment device 100 is inserted into a hole in the bone. For example, after the attachment device 100 is inserted into a hole in the bone, the network of pores extending from the groove surfaces 118 remains unclogged and intact due to the recessed configuration of the groove surfaces 118. As a result, bone may rapidly grow into the first portion 102 to fuse the attachment device 100 to the bone. Advantageously, the grooves 116 may be packed with bone growth-promoting material, such as morselized bone or BMP, prior to being inserted into a hole in a bone.

Figure 8:
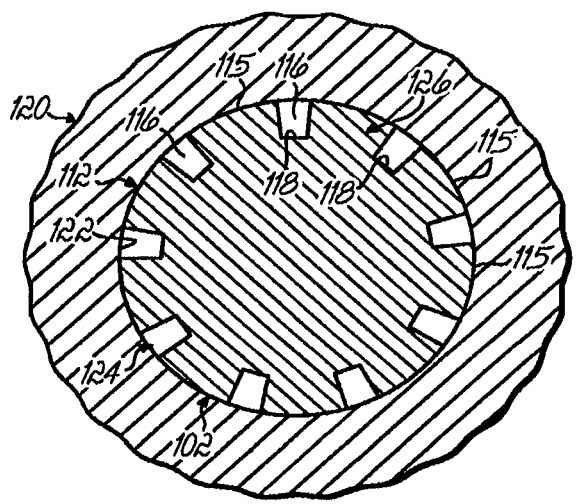
FIG. 8 is a cross-sectional view of the attachment device of FIG. 7 secured within a hole in a bone.

FIG. 8 illustrates a cross-section of the attachment device 100 when inserted into a hole 122 extending through an outer layer of cortical bone 120. The outer surface 112 defines a plurality of bone-engaging surfaces 115 in contact with the cortical bone 82. Conversely, the grooves 116 are not in contact with the cortical bone 120 allowing for bone in-growth or enabling the grooves 116 to be filled with bone growth-promoting materials. Thus, in this embodiment, the grooves 116 collectively define a bone in-growth portion of the attachment device 40 and the remainder of the attachment device 40, including the bone-engaging surfaces 115, defines an interference fit portion 126.

Figure 9:
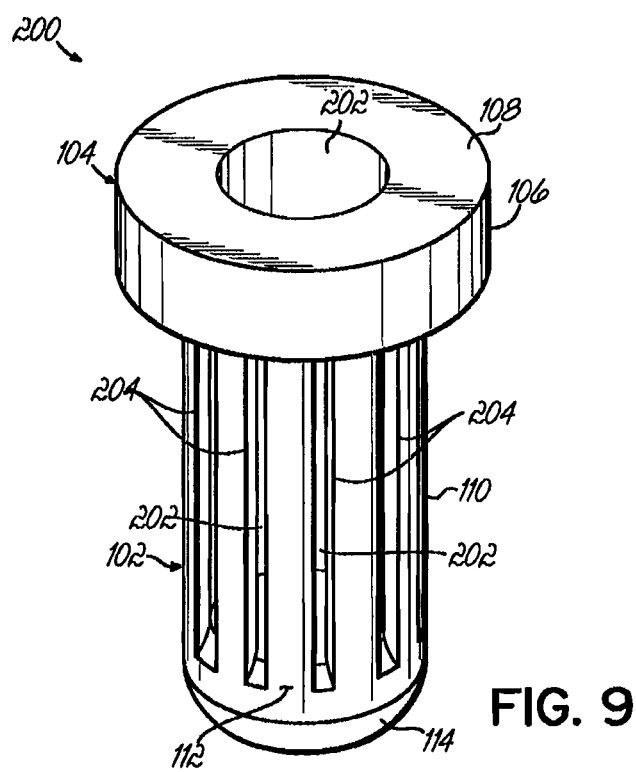
FIG. 9 is a perspective view of an attachment device according to yet another embodiment of the invention.

FIG. 9 illustrates an attachment device 200 according to yet another embodiment of the invention. Because the attachment device 200 is substantially similar to the attachment device 100, like reference numbers are used to refer to like structure and only the differences between the two embodiments will be discussed below.

In particular, the attachment device 200 further includes a bore 202 extending through the second portion 104 and into the first portion 102. Instead of or in addition to including the grooves 116, one or more channels 204 are provided along at least a portion of the first portion 102. Each channel 204 extends from the outer surface 112 to the bore 202. As a result, morselized bone, BMP, or other material designed to promote bone growth may be delivered to the channels 204 through the bore 202 before, during, or after the attachment device 200 is inserted into a hold in a bone. If desired, the bore 202 may extend completely through both the main body section 110 and bottom section 114 of the first portion 102.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, the first portion 42 may alternatively have a circular cross-sectional profile when viewed in a plane perpendicular to the axis 45. Additionally, the attachment device 40 need not be symmetrical about the axis 45 as it is shown. In other embodiments, the implant can be a plate, such as a cervical plate, configured for attachment to a vertebral body. One exemplary plate is shown in U.S. Pat. No. 6,890,335, the disclosure of which is fully incorporated herein by reference. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of stabilizing a facet of a patient with a porous fixation device having a first portion and a second portion, the first portion comprising a porous material, the second portion having a width greater than a width of the first portion, the width measured perpendicular to a longitudinal axis of the porous fixation device, the method comprising:
    creating a hole in a portion of a facet;
    inserting the porous fixation device into the hole in the facet such that the first portion is within the hole and the second portion is exterior of the hole; wherein the first portion comprises a material with a first porosity and the second portion comprises a material with a second porosity, wherein the second porosity is less than the first porosity.

2. The method of claim 1, wherein the first portion includes a plurality of grooves in an outer surface thereof.

3. The method of claim 2, wherein creating a hole in a portion of the facet involves creating a hole sized such that the first portion of the porous fixation device has an interference fit within the hole.

4. The method of claim 3, further comprising packing the grooves with bone growth-promoting material before inserting the fixation device into the hole.

5. The method of claim 4, wherein the bone growth-promoting material is morselized bone.

6. The method of claim 4, wherein the bone growth-promoting material is bone morphogenetic protein.

7. The method of claim 1, wherein the porous material has a degree of porosity that approaches that of natural cancellous bone.

8. The method of claim 7, wherein the porous material is a porous metal.

9. The method of claim 8, wherein the porous material is porous tantalum.

10. The method of claim 7, wherein the porous material is porous ceramic.

11. The method of claim 1, wherein the step of inserting the fixation device into the hole includes inserting the fixation device through an opening in an implant and then into the hole, such that the fixation device attaches the implant to the facet.

12. A method of treating a spine of a patient with a porous fixation device having a first surface and a second surface, the method comprising:

creating a hole in a portion of a facet sized to have an interference fit with the first surface of the fixation device;

inserting the porous fixation device into the hole in the facet such that the first surface is within the hole and in contact with an inner surface of the hole, while the second surface is not in contact with the inner surface of the hole, wherein the porous fixation device further includes an exterior portion that remains outside the hole when the fixation device is inserted into the hole, wherein the porous fixation device comprises a material with a first porosity and the exterior portion comprises a material with a second porosity, wherein the second porosity is less than the first porosity.

13. The method of claim 12, wherein the second surface comprises one or more indentations in the first surface.

14. The method of claim 13, further comprising packing the indentations with bone growth-promoting material before inserting the fixation device into the hole.

15. The method of claim 14, wherein the bone growth-promoting material is morselized bone or bone morphogenetic protein.

16. The method of claim 12, wherein the porous material has a degree of porosity that approaches that of natural cancellous bone.

17. The method of claim 16, wherein the porous material is a porous metal.

18. The method of claim 17, wherein the porous metal is porous tantalum.

19. A method of stabilizing a facet of a patient with a porous fixation device having a first portion and a second portion, the first portion comprising a porous material, the method comprising:

creating a hole in a portion of a facet;

inserting the porous fixation device into the hole in the facet such that the first portion is within the hole and the second portion is exterior of the hole, wherein the first portion comprises a material with a first porosity and the second portion comprises a material with a second porosity, wherein the second porosity is less than the first porosity.

* * * * *